US006100432A

United States Patent [19]
Borgel et al.

[11] Patent Number: 6,100,432
[45] Date of Patent: Aug. 8, 2000

[54] PROCESS FOR RECYCLING A LIQUID HYDROFORMYLATION DISCHARGE

[75] Inventors: Franz Borgel, Dirmstein; Rolf Müller, Dannstadt-Schauernheim; Roland Krokoszinski, Weisenheim, all of Germany

[73] Assignee: BASF Aktiengesellschaft, Ludwigshafen, Germany

[21] Appl. No.: 09/000,055

[22] PCT Filed: Aug. 21, 1996

[86] PCT No.: PCT/EP96/03665

§ 371 Date: May 29, 1998

§ 102(e) Date: May 29, 1998

[87] PCT Pub. No.: WO97/07086

PCT Pub. Date: Feb. 27, 1997

[30] Foreign Application Priority Data

Aug. 21, 1995 [DE] Germany .................... 195 30 698

[51] Int. Cl.⁷ .................................................. C07C 45/50
[52] U.S. Cl. ........................................ 568/454; 568/451
[58] Field of Search ...................... 568/454, 451

[56] References Cited

U.S. PATENT DOCUMENTS 3,455,091  7/1969  Herber et al. .
4,148,830  4/1979  Pruett et al. .
5,001,274  3/1991  Bunning .................................. 568/454

FOREIGN PATENT DOCUMENTS 16 286   10/1980  European Pat. Off. .
188 246   7/1986  European Pat. Off. .
404 193  12/1990  European Pat. Off. .
423 769   4/1991  European Pat. Off. .
484 976   5/1992  European Pat. Off. .

*Primary Examiner*—Shailendra Kumar
*Assistant Examiner*—Sreeni Padmanabhan
*Attorney, Agent, or Firm*—Keil & Weinkauf

[57] ABSTRACT

A process for the purification of a substantially liquid effluent containing aldehydes and unconverted olefins coming from a hydroformylation reactor following low-pressure hydroformylation of $C_2$–$C_{20}$ olefins or olefin mixtures containing different isomers of the respective olefins, said hydroformylation being catalyzed by means of a phosphorous rhodium catalyst homogeneously dissolved in the reaction medium and carried out at a temperature of from 50° to 150° C. and a pressure of from 2 to 30 bar.

5 Claims, 1 Drawing Sheet

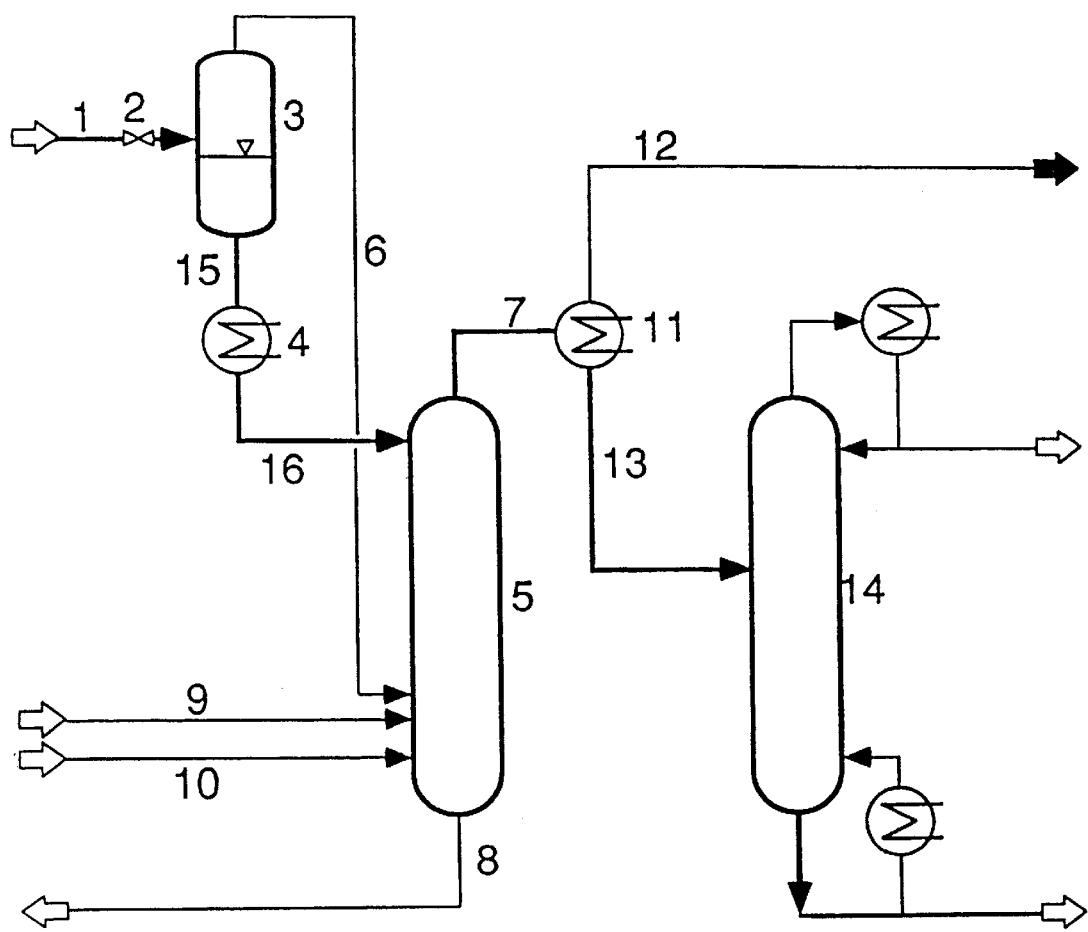

PROCESS FOR RECYCLING A LIQUID HYDROFORMYLATION DISCHARGE

This is the U.S. National Stage Application of PCT/EP96/03665 filed Aug. 21, 1996, now WO 97/07086, published Feb. 27, 1997.

DESCRIPTION

The present invention relates to a process for the purification of a substantially liquid effluent containing aldehydes and unconverted olefins coming from a hydroformylation reactor following low-pressure hydroformylation of $C_3-C_{20}$ olefins or olefin mixtures containing different isomers of the respective olefins, said hydroformylation being catalyzed by means of a phosphorous rhodium catalyst homogeneously dissolved in the reaction medium and carried out at a temperature of from 50° to 150° C. and a pressure of from 2 to 30 bar.

The hydroformylation of olefins to form the corresponding aldehydes is of very great economical significance, since the aldehydes prepared in this way are in turn starting materials for a large number of commercial products such as solvents or plasticizer alcohols. Hydroformylation processes are accordingly subjected to intensive research world-wide, in order to achieve further economical improvements, for example in the energy balance of the process, to increase its selectivity, and to protect the homogeneous rhodium catalyst.

The so-called liquid-discharge process is generally used for the hydroformylation of $C_3-C_{20}$ olefins to produce the corresponding aldehydes (U.S. Pat. No. 4,148,830, EP-A 16,286) in which the substantially liquid—except for the synthesis gas used in excess to effect hydroformylation—effluent from the hydroformylation reactor is depressurized in a let-down vessel, the effluent, on account of the pressure drop, being separated into a liquid phase containing the catalyst, solvent, high-boiling by-products and a minor amount of aldehyde and unconverted olefin and a gas phase containing, in addition to the excess synthesis gas, the major portion of aldehyde formed and the unconverted olefin. The liquid phase is then recycled to the reactor as return stream and the gas phase is withdrawn, the synthesis gas separated therefrom and the mixture subsequently separated into aldehyde and olefins by distillation. The liquid return stream contains amounts of aldehyde and olefin which are small compared with the gas stream withdrawn from the let-down tank but which are not negligible with respect to the economic value of the process. Apart from the fact that it is uneconomical to circulate a specific amount of aldehyde in such manner constantly, the recycled aldehyde tends to form high-boiling condensation products under the hydroformylation conditions. Although the latter are good solvents for said hydroformylation, it is desirable, for economical reasons, to keep the reformation of such high-boiling by-products within narrow limits. Recycling of residual amounts of olefin dissolved in the liquid return stream can also be disadvantageous when the starting material used for the hydroformylation is not a pure olefin but a hydrocarbon mixture containing, in addition to the olefin to be converted, other isomeric olefins and saturated hydrocarbons.

For the aforementioned reasons it would be advantageous to distil the liquid phase separated in the let-down vessel prior to recycling to the hydroformylation reactor, to effect separation of residual amounts of aldehyde or olefin. Such a procedure is however uneconomical, since to effect distillation of the liquid phase from the let-down vessel said liquid phase must be heated strongly. Prior to recycling to the hydroformylation reactor the said heated liquid phase would have to be cooled down, since otherwise the temperature in the hydroformylation reactor would rise to unduly high values due to the heat of reaction liberated in the hydroformylation reactor. Thus such a process would be very unsatisfactory when regarded from the energy balance point of view.

In the prior art (EP-A 404,193, EP-A 484,976) the liquid phase separated in the let-down tank is used as absorbent for those unconverted olefins which become gaseous in the let-down tank. For this purpose the gas phase is passed, in an absorption column, through the (cooled) liquid phase having a temperature not higher than that in the let-down tank, and the olefins present in this gas stream are entirely or partially absorbed by said liquid phase. The liquid phase thus laden with olefins is then either directly returned to the hydroformylation reactor or freed from the olefins in separate desorption equipment. These processes are, for the above reasons, particularly disadvantageous when the starting material used is an olefin mixture of isomeric olefins.

It is thus an object of the present invention to provide an economical process for the hydroformylation of olefins, in particular of the olefin mixtures such as are commercially obtained, for example, as refined product II from steam crackers following separation of the 1,3-butadiene and isobutene present therein, in which the aforementioned drawbacks regarding further purification of the liquid effluent from the hydroformylation reactor are avoided.

Accordingly, we have found a process for the purification of a substantially liquid effluent containing aldehydes and unconverted olefins coming from a hydroformylation reactor following low-pressure hydroformylation of $C_2-C_{20}$ olefins or olefin mixtures containing different isomers of the respective olefins, said hydroformylation being catalyzed by means of a phosphorous rhodium catalyst homogeneously dissolved in the reaction medium and carried out at a temperature of from 50° to 150° C. and a pressure of from 2 to 30 bar, wherein a) the hydroformylation product stream containing liquid and gaseous components and comprising, apart from the catalyst, essentially the hydroformylation product, by-products boiling at temperatures above the boiling point of the hydroformylation product, unconverted olefin, and saturated hydrocarbons and unconverted synthesis gas, is depressurized in a let-down vessel, b) during depressurization, the pressure and temperature are lowered to such a degree that there are formed a liquid phase containing essentially the catalyst, by-products boiling at temperatures higher than the boiling point of the hydroformylation product, and residual amounts of hydroformylation product and unconverted olefin, and a gas phase containing essentially the hydroformylation product, unconverted olefin, saturated hydrocarbons, and unconverted synthesis gas, c) a liquid stream is withdrawn from said liquid phase, and a gaseous stream is withdrawn from said gas phase, d) the liquid stream is then heated to a higher temperature than the temperature prevailing in the let-down vessel, e) the heated liquid stream is passed in liquid form to the head region or the upper part of a column, f) the said gaseous stream withdrawn from the let-down vessel is passed to the bottom or lower part of said column and caused to flow countercurrently to the liquid stream introduced at the head or upper part of this column, g) a gaseous stream enriched in olefin and hydroformylation product is withdrawn at the head of the column and passed on for further purification, h) a liquid stream is withdrawn at the bottom of said column, which stream contains less hydroformylation product and olefin than present in the liquid stream fed to the head region or upper part the column, and i) all or part of this liquid stream is recycled to the hydroformylation reactor.

The process of the invention is illustrated below with reference to the attached drawing and the reference numbers contained therein. The drawing is a purely diagrammatic flow sheet designed only for illustration of the process of the invention, in which, for reasons of clarity, only that equipment is shown which is necessary to illustrate the process, whilst other units obviously necessary for the execution of the process, such as pumps, additional valves, relays, etc. are omitted from the drawing.

In the process of the invention, the substantially liquid effluent from the hydroformylation reactor, which generally has a temperature of from 50° to 150° C. and preferably from 80° to 110° C. and is under a pressure generally of from 2 to 30 bar and preferably from 10 to 25 bar, is passed through pipe line 1 to be depressurized, via valve 2, in the let-down vessel 3.

At the temperature and pressure stated, the synthesis gas used in excess to effect hydroformylation—a carbon monoxide/hydrogen mixture having a molar ratio of CO to $H_2$ of generally from 20:80 to 80:20, preferably from 40:60 to 60:40—is present in the gaseous state mostly in the form of fine bubbles of gas suspended in the otherwise liquid effluent coming from the hydroformylation reaction. Under these conditions, a minor portion of the unconverted synthesis gas is dissolved in the liquid effluent.

The liquid part of the effluent from the hydroformylation reaction contains, as essential components, the rhodium catalyst, the hydroformylation product, ie the aldehyde(s) produced from the olefin or olefin mixture used, condensation products of these aldehydes which boil at higher temperatures than the hydroformylation product, as formed as by-products during the hydroformylation and whose composition and manner of formation are described, eg, for condensation products of butyraldehyde, in U.S. Pat. No. 4,158,830, or as present from the outset in the hydroformylation reactor as solvent for the hydroformylation reaction, unconverted olefin(s) and any unconverted, ie unreactive, saturated hydrocarbons.

The hydrocarbons may have been entrained into the hydroformylation reactor with the starting material used for the hydroformylation, but a portion thereof may have formed in a side reaction taking place at the same time as the hydroformylation, ie the hydrogenation of the olefins.

The rhodium catalyst present in the hydroformylation product stream is a complex with one or more organophosphoric compounds as ligands, which complex is homogeneously soluble in the reaction medium of the hydroformylation reaction.

As examples of such ligands there may be mentioned phosphine ligands of the types: triaryl phosphine, $C_1$–$C_6$ alkyldiaryl phosphine or arylalkyl diphosphine, such as cyclohexyldiphenyl phosphine, hexyldiphenyl phosphine, tritolyl phosphine, tetraphenyidiphosphinomethane, 1,2-bis (diphenyl phosphino)ethane, 1,3-bis(di-phenyl phosphino) propane, 1,4-bis(diphenyl phosphino)butane, in particular triphenyl phosphine, and also the bisphosphine ligands described in EP-A 279,018, EP-A 311,619, WO 90/06810, and EP-A 71,281, or sterically hindered phosphite ligands, such as the chelating phosphite ligands described in U.S. Pat. No. 4,668,651, U.S. Pat. No. 4,748,261, U.S. Pat. No. 4,769,498, U.S. Pat. No. 4,774,361, U.S. Pat. No. 4,835,299, U.S. Pat. No. 4,885,401, U.S. Pat. No. 5,059,710, U.S. Pat. No. 5,113,022, U.S. Pat. No. 5,179,055, U.S. Pat. No. 5,260,491, U.S. Pat. No. 5,264,616, U.S. Pat. No. 5,288,918, U.S. Pat. No. 5,360,938, EP-A 472,071 and EP-A 518,241, and also triphenyl phosphites substituted by in each case 1 or 2 isopropyl groups and/or tert-butyl groups on the phenyl ring, preferably in ortho position to the phosphite ester grouping. Since the aforementioned ligands are used in a molar excess over the rhodium generally to an extent of from 10 to 1000 times, preferably from 50 to 500 times, and such an excess of the ligands over the rhodium is significant for the activity, selectivity, and stability of the rhodium catalyst, the mixture of the rhodium complex with the ligand and the free ligand is designated simply as "rhodium catalyst" or "catalyst" for the purposes of this application.

The above statements concerning the hydroformylation process and the rhodium catalyst used therein serve to place the process of the invention in its overall commercial context by way of illustration. It may be emphasized at this juncture that the hydroformylation preceding the process of the invention may be carried out in the manner of known and commonly used hydroformylation processes giving a liquid effluent known in the art, for example by the process according to U.S. Pat. No. 4,148,830, EP-A 16,286, EP-A 188,246 or EP-A 423,769, and the particular form of said hydroformylation used is not subject matter of the present invention.

The depressurization of the substantially liquid hydroformylation product stream in let-down vessel 3 causes the separation of the substantially liquid hydroformylation product stream into a liquid phase which contains essentially the catalyst, by-products produced during the hydroformylation reaction and boiling at higher temperatures than the hydroformylation product, residual amounts of olefin, and hydroformylation product and, if an additional high-boiling solvent was used in the hydroformylation, said solvent, and into a gas phase essentially containing the major portion of the hydroformylation product, the major portion of the unconverted olefin, saturated hydrocarbons, and unconverted synthesis gas. Since the hydroformylation products produced depending on the olefinic starting material used, ie aldehydes, or mixtures of straight-chain products (n-aldehydes) or branched-chain products (isoaldehydes), have a different vapor pressure, it will be apparent to the person skilled in the art that the pressure and the temperature in the let-down vessel must be adjusted with respect to the vapor pressure of the particular hydroformylation product present, such that the major portion of the hydroformylation product changes from liquid phase to gas phase during depressurization of the liquid hydroformylation product stream in the let-down vessel.

Generally, the pressure and temperature in the let-down vessel are adjusted such that the liquid phase separated in the let-down vessel generally contains not more than 10 to 30 wt % of hydroformylation product and generally not more than 0.1 to 10 wt % of olefin or olefins. The complete transformation of the hydroformylation product and unconverted olefins into the gas phase in the let-down vessel is not generally economically feasible. In order to achieve such a distribution of the hydroformylation product and unconverted olefins between the gas phase and the liquid phase in the let-down vessel, the vapor pressure of the respective hydroformylation product must be considered when determining the pressure and temperature conditions in the let-down vessel: for example, in the purification of the liquid effluent from the hydroformylation of refined product II—a mixture of 1-butene, 2-butenes, and butanes such as is obtained following removal of the 1,3-butadiene and isobutene present therein—which contains, in addition to the unconverted olefins and hydrocarbons, n-valeraldehyde and isovaleraldehyde as hydroformylation product, the hydroformylation product stream is depressurized in the let-down vessel to a pressure of generally 1–5 bar, preferably 1–3 bar, whilst the temperature in the let-down vessel generally attains a value of from 50° to 150° C., preferably 70° to 90° C., due to the pressure drop and evaporation of the respective components.

The liquid phase separated in the let-down vessel 3 is withdrawn from the let-down vessel as a liquid stream through pipe line 15 and this stream is heated, for example by means of a continuous flow heater or heat exchanger 4, to a temperature which is generally from 10° to 80° C. higher than the temperature of the liquid phase in the let-down vessel 3. Basically, it is also possible to heat the liquid phase separated in the let-down vessel by means of heating equipment installed on or in the let-down vessel to a temperature which is higher, by said amount, than the temperature at which the liquid phase was separated in the let-down vessel separated without heating the let-down vessel. Advantageously however, the liquid stream withdrawn from the let-down vessel is heated to the desired temperature.

The thus heated liquid stream coming from the let-down tank is passed through pipe line 16 to the head region or upper part of a column 5 advantageously packed with, eg, a ring packing, a spiral packing, or a saddle packing, or other packing or internal fittings such as trickle plates, for the purpose of creating a large surface area in the column. In said column the said liquid stream flows countercurrently to the gas stream withdrawn from the upper part the let-down vessel 3 and fed to the lower part the column 5 via pipe line 6 and consisting of the gas phase formed in the let-down vessel. The intimate contact achieved between the gas stream and the heated liquid stream, improved by the large surface area present in the column, causes the residual amounts of hydroformylation product and unconverted olefin present in the liquid stream to be transferred to the gas stream such that the gas stream removed from the head of the column 5 via pipe line 7 is, compared with the gas stream introduced at the lower end of the column, enriched in hydroformylation product and unconverted olefin, whilst the liquid stream leaving the bottom of the column 5 via pipe line 8 contains less hydroformylation product and unconverted olefin than the liquid stream fed to the head region or upper part of the column 5.

This result is very surprising and unexpected, since the gas stream introduced at the lower end of the column already contains the major portion of the hydroformylation product and unconverted olefin present in the liquid hydroformylation product stream, ie that portion transferred to the gas phase in the let-down vessel. Due to the high content of hydroformylation product and unconverted olefin in the gas stream introduced at the lower end of the column 5 and the low content of hydroformylation product and unconverted olefin in the liquid stream fed to the top or upper part of the column 5, it would have been expected that the hydroformylation product and unconverted olefin present in the gas stream in high concentration would have been absorbed by the liquid stream until a state of equilibrium were reached.

The liquid stream leaving the column 5 via the bottom and pipe line 8 has a very low content of hydroformylation product and unconverted olefin and consists of essentially the catalyst and by-products of the hydroformylation reaction boiling at higher temperatures than the hydroformylation product and may optionally contain a high-boiling solvent additionally used in the hydroformylation, and a portion of this stream or the entire stream is recycled to the hydroformylation reactor (not shown). Advantageously a partial stream is usually tapped off from this liquid return stream, continuously or batchwise, for the purpose of removing spent catalyst (not shown). The impoverishment factor, ie the ratio of the concentration of the hydroformylation product in the liquid stream fed to column 5 to the concentration of the hydroformylation product in the liquid stream withdrawn at the bottom of column 5, is generally from 1.01 to 3.

The gas stream withdrawn at the head of column 5 via pipe line 7 and enriched in the hydroformylation product and unconverted olefin, which contains, as additional noteworthy components, saturated hydrocarbons and unconverted synthesis gas, is advantageously passed to a condenser 11 for further purification, in which its higher-boiling components—the hydroformylation product, unconverted olefin, saturated hydrocarbons—are separated by condensation from the unconverted synthesis gas.

The resulting separated unconverted synthesis gas is removed via pipe line 12 and can, if desired, following compression to the pressure of the hydroformylation reaction, be recycled to the hydroformylation reactor. If desired, fresh synthesis gas may be additionally introduced, or the unconverted synthesis gas removed, via pipe line 12 through pipe line 9 at the lower end of the column, before the aforementioned stream of synthesis gas is passed back to the hydroformylation reactor in its entirety or as a partial stream after separation of the condensable components. Such an additional measure is not necessary, however, for the successful operation of the process of the invention.

The condensable components of the gas stream removed from column 5 via pipe line 7, separated in the condenser 11 and essentially comprising the hydroformylation product, unconverted olefin, and saturated hydrocarbons is fed via pipe line 13 to a distillation plant 14 (shown diagrammatically), which can be composed of a number of distillation plants, and is fractionated into its individual components, which can subsequently be passed on for further processing to other desired products. This distillation can be carried out by any conventional process known in the art and its particular form is not subject matter of the process of the invention.

The purifying process of the invention is basically suitable for the purification of liquid effuents from rhodium-catalyzed hydroformylation of olefins, which, due to their material properties and due to the material properties of the hydroformylation products formed therefrom, are suitable for use in a hydroformylation process giving a liquid effluent of the hydroformylation mixture. These are generally $C_2$–$C_{20}$ olefins. The purifying process of the invention is preferably used for the purification of liquid hydroformylation effluents from the hydroformylation of $C_2$–$C_{10}$ olefins and more preferably $C_2$–$C_5$ olefins, preferably monoolefins. The olefins used can be unsubstituted or they can be substituted by one or two, preferably one, substituent(s) inert under the hydroformylation conditions, for example an ester group, nitrile group, alkoxy group, or hydroxy group.

If the rhodium catalyst used for the hydroformylation is a complex of rhodium with a phosphine ligand, generally virtually only 1-butene is hydroformulated to n- and iso-valeraldehydes under the aforementioned conditions of the hydroformylation reaction. If, on the other hand, the rhodium catalyst used in the hydroformylation process is a complex of rhodium with a sterically hindered phosphite ligand, 2-butene is isomerized in the hydroformylation reactor in situ to form 1-butene, which is then hydroformylated to n- and iso-valeraldehydes.

The liquid effluent from the hydroformylation reactor is then, as stated, depressurized in the let-down vessel 3, this producing a liquid phase containing, as essential components, the rhodium catalyst, higher-boiling condensation products of n- and iso-valeraldehydes, optionally a further solvent, and also residual amounts of unconverted butenes, and a gas phase containing, as essential components, the major portion of the n- and iso-valeraldehydes formed in the hydroformylation, the major portion of the unconverted butenes, ie the isobutene still present in the refined product II in traces, and, depending on the type of rhodium catalyst used in the hydroformylation reaction, optionally 2-butene and at most, small amounts of 1-butene or optionally, depending on the rhodium catalyst, small amounts of 2-butene, as well as various butane isomers and unconverted synthesis gas.

From the liquid phase which separates in the let-down vessel 3 there is continuously withdrawn, via pipe line 15, a liquid stream, the temperature of which is raised in a heat exchanger 4, preferably by from 20° to 80° C., and which, on passing through the heat exchanger 4, is fed via pipe line 16 to the head region or upper part of column 5. From the gas phase separated in the let-down tank 3 there is continuously withdrawn, via pipe line 6, a gas stream, which is pumped, preferably without further heating, to the bottom or the lower part of column 5 and is allowed to flow countercurrently to the liquid stream fed to the head region or upper part of column 5. At the bottom of the column there is withdrawn, via pipe line 8, a liquid stream which has a very low content of, or is free from, valeraldehydes and which contains the rhodium catalyst and the higher boiling condensation products of the isomeric valeraldehydes and optionally a further high-boiling solvent, and is recycled to the hydroformylation reactor either in its entirety or following removal of a partial stream for working up spent rhodium catalyst. At the top of column 5 a gas stream enriched in valeraldehydes and unconverted olefins is removed and passed through pipe line 7 to the condenser 11, in which its condensable components, essentially n- and iso-valeraldehydes, isobutene, butanes, and, depending on the catalyst used in the hydroformylation, greater or smaller amounts of 2-butene and also residual amounts of 1-butene, are condensed and passed on to distillative purification via pipe line 13. The unconverted synthesis gas cannot be condensed in the condenser 11 and is recycled, either completely or in part, to the hydroformylation reactor via pipe line 12 following compression. In the purification by distillation of the liquid condensate obtained in the condenser 11 the readily volatile butenes and butanes are advantageously first separated from the valeraldehyde mixture and subsequently separated into the individual components isobutene, optionally 2-butenes, butene-1, and butanes. The 2-butene and the residual amounts of 1-butene can be used for butene dimerisation and the butanes can be used as starting material in a steam cracker. The n-iso-valeraldehyde mixture obtained can if desired be separated into the individual isomers or used as such for the preparation of the plasticizer alcohol 2-propylheptanol. If desired the gaseous butenes separated by distillation, ie the exhaust gas of the process, may be recycled via pipe line 10 to the column 5, completely or as a partial stream.

The process of the invention provides better and more complete separation of the aldehydes present in the liquid hydroformylation product stream from the other components in a more economical manner than in the prior art. In particular, the process of the invention provides the isolation of the hydroformylation products from the liquid hydroformylation product stream with substantially less energy consumption than in known processes. On account of the mild conditions used in the process of the invention for the purification of the liquid hydroformylation product stream, the rhodium catalyst is protected and there are formed, during purification, fewer by-products derived from the hydroformylation product, by which means the overall selectivity of the process and thus its economic value are improved.

What is claimed is:

1. A process for the purification of a substantially liquid effluent containing aldehydes and uncoverted olefins coming from a hydroformylation reactor following low-pressure hydroformylation of $C_2$–$C_{20}$ olefins or olefin mixtures containing different isomers of the respective olefins, said hydroformylation being catalyzed by means of a phosphorous rhodium catalyst homogeneously dissolved in the reaction medium and carried out at a temperature of from 50° to 150° C. and a pressure of from 2 to 30 bar, wherein a. the hydroformylation product stream containing liquid and gaseous components and comprising, apart from the catalyst, essentially the hydroformylation product, by-products boiling at temperatures above the boiling point of the hydroformylation product, unconverted olefin, and saturated hydrocarbons and unconverted synthesis gas, is depressurized in a let-down vessel, b. during depressurization, the pressure and temperature are lowered to such a degree that there are formed a liquid phase containing essentially the catalyst, by-products boiling at temperatures higher than the boiling point of the hydroformylation product, and residual amounts of hydroformylation product and unconverted olefin, and a gas phase containing essentially the hydroformylation product, unconverted olefin, saturated hydrocarbons, and unconverted synthesis gas, c. a liquid stream is withdrawn from said liquid phase, and a gaseous stream is withdrawn from said gas phase, d. the liquid stream is then heated to a temperature which is from 10° to 80° higher than the temperature prevailing in the let-down vessel, e. the heated liquid stream is passed in liquid form to the head region or the upper part of a column, f. the said gaseous stream withdrawn from the let-down vessel is passed to the bottom or lower part of said column and caused to flow countercurrently to the liquid stream introduced at the head or upper part of this column, g. a gaseous stream enriched in olefin and hydroformylation product is withdrawn at the head of the column and passed on for further purification, h. a liquid stream is withdrawn at the bottom of said column, which stream contains less hydroformylation product and olefin than present in the liquid stream fed to the head region or upper part of the column, and i. all or part of this liquid stream is recycled to the hydroformylation reactor.

2. A process as defined in claim 1, wherein ethylene is used as olefin and propionaldehyde is produced.

3. A process as defined in claim 1, wherein propylene is used as olefin and n- and iso-butanols are produced.

4. A process as defined in claim 1, wherein 1-butene or a 1-butene-containing hydrocarbon mixture is used as olefin and n- and iso-valeraldehydes are produced.

5. A process as defined in claim 1, further comprising feeding (1) fresh or recycled synthesis gas or (ii) exhaust gas from the process, or a mixture of (i) and (ii), is additionally fed to the bottom region of the column.

* * * * *